(12) United States Patent
Gabbay

(10) Patent No.: US 7,311,730 B2
(45) Date of Patent: Dec. 25, 2007

(54) SUPPORT APPARATUS AND HEART VALVE PROSTHESIS FOR SUTURELESS IMPLANTATION

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 10/778,278

(22) Filed: Feb. 13, 2004

(65) Prior Publication Data

US 2005/0182486 A1 Aug. 18, 2005

(51) Int. Cl.
*A61F 2/24* (2006.01)

(52) U.S. Cl. .................. 623/2.38; 623/1.24; 623/2.14; 623/2.17; 623/2.23; 606/153

(58) Field of Classification Search ............... 623/1.14, 623/1.36, 2.11, 2.14, 2.17, 2.18, 2.23, 2.36–2.4, 623/900, 1.24, 2.1; 606/153
See application file for complete search history.

(56) References Cited

U.S. PATENT DOCUMENTS

| 3,686,740 | A | | 8/1972 | Shiley | |
|---|---|---|---|---|---|
| 5,234,447 | A | | 8/1993 | Kaster et al. | |
| 5,370,685 | A | * | 12/1994 | Stevens | 623/2.11 |
| 6,197,054 | B1 | * | 3/2001 | Hamblin et al. | 623/2.38 |
| 6,458,153 | B1 | * | 10/2002 | Bailey et al. | 623/1.24 |
| 7,097,659 | B2 | * | 8/2006 | Woolfson et al. | 623/2.4 |
| 2001/0049555 | A1 | * | 12/2001 | Gabbay | 623/2.13 |
| 2002/0032481 | A1 | * | 3/2002 | Gabbay | 623/2.11 |
| 2002/0055774 | A1 | * | 5/2002 | Liddicoat | 623/2.4 |

FOREIGN PATENT DOCUMENTS

SU 1697790 A1 * 12/1991
WO WO 0044311 A2 * 8/2000

OTHER PUBLICATIONS

"PCT International Search Report", SHE-6898-PCT, PCT/US05/04647, Feb. 12, 2005.

* cited by examiner

*Primary Examiner*—Corrine McDermott
*Assistant Examiner*—Javier G. Blanco
(74) *Attorney, Agent, or Firm*—Tarolli, Sundheim, Covell & Tummino LLP

(57) ABSTRACT

An apparatus is disclosed for supporting a heart valve at an annulus of an implantation site. The apparatus includes a base portion operative to maintain a circumferential dimension thereof. A plurality of fingers extend axially and radially outwardly from the first end of the support element. A heart valve can be located within the apparatus to provide a prosthesis that can be suturelessly implanted at an annulus of a patient.

13 Claims, 8 Drawing Sheets

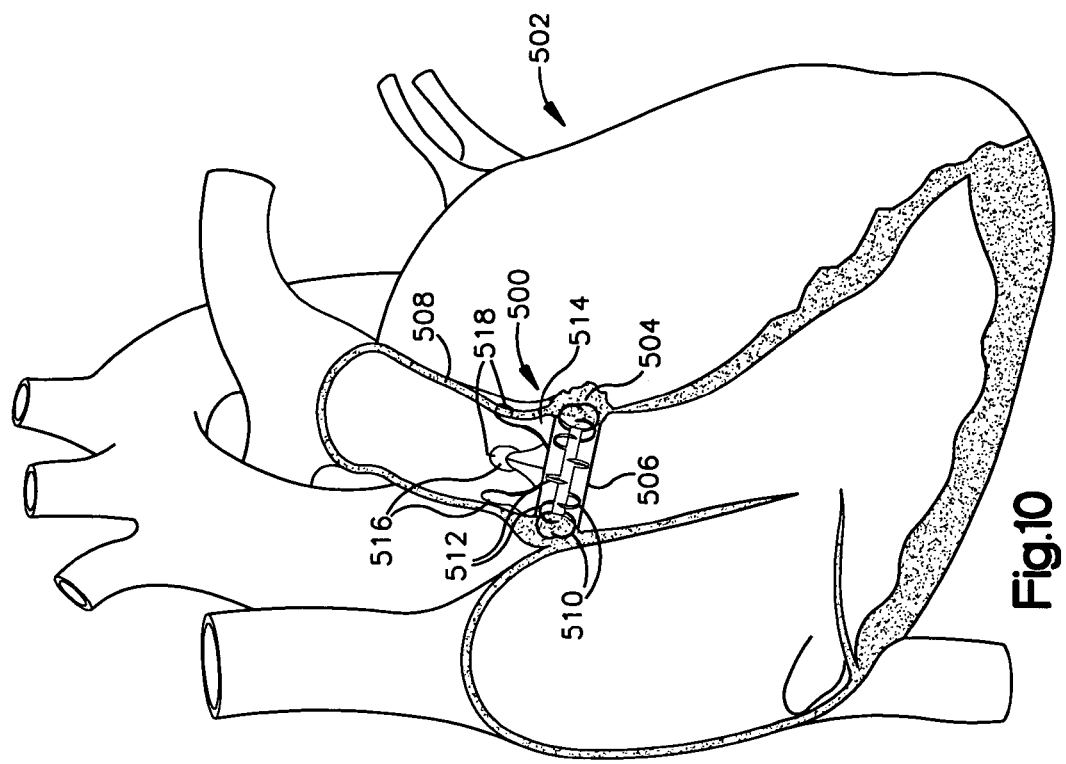
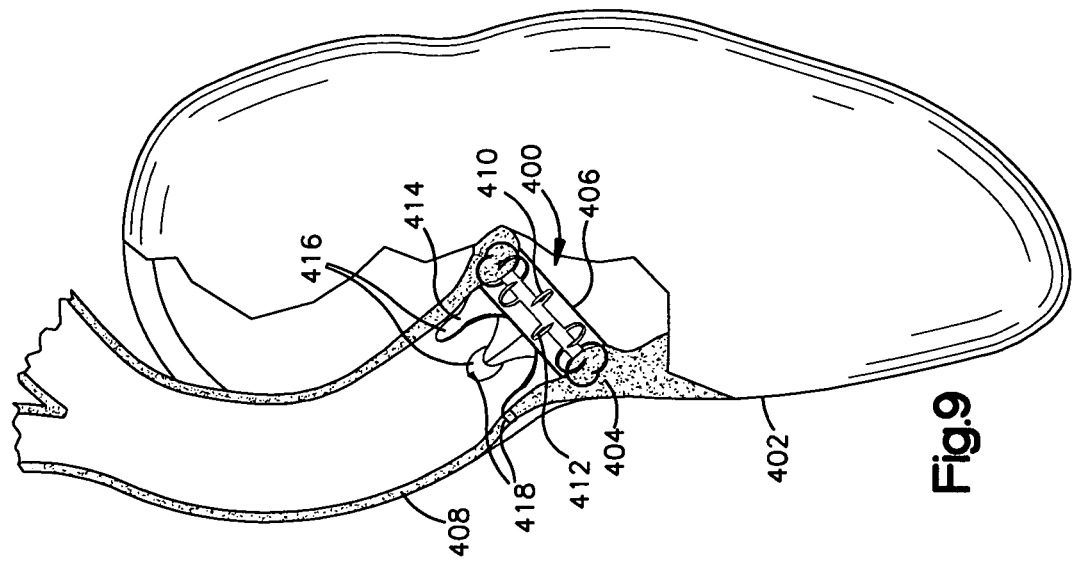

SUPPORT APPARATUS AND HEART VALVE PROSTHESIS FOR SUTURELESS IMPLANTATION

TECHNICAL FIELD

The present invention relates to an implantable apparatus and, more particularly, to a support apparatus and heart valve prosthesis that does not require sutures for implantation.

BACKGROUND

It is well known to utilize mechanical heart valves, such as a ball check valve, and natural tissue cardiac valves to replace defective aortic and mitral valves in human patients. One type of natural tissue heart valve typically employs a porcine valve for implantation in a human, as they are very similar to human valves of appropriate size and generally are easy to procure. Typically, the porcine valve is fixed by chemically treating it, such as with an appropriate glutaraldehyde solution. The treated porcine valve further may be mounted into a stent to support the valve at a fixed position.

In order to surgically implant a heart valve into a patient, the patient typically is placed on cardiopulmonary bypass during a complicated, but common, open chest procedure. In certain situations, an individual requiring a heart valve replacement may be substantially ill, such that placing the individual on cardiopulmonary bypass for an extended period of time may pose too great of risk. In particular, many older patients having a deficient aortic or pulmonic valve may be too ill to survive conventional open-heart surgery. Patients exhibiting these and other conditions would benefit from an improved heart valve prosthesis that may be implanted by a more efficient implantation procedure.

SUMMARY

One aspect of the present invention provides a support apparatus to facilitate implantation of a heart valve prosthesis. The support apparatus includes a base portion curved about an axis, the base portion having axially spaced apart first and second ends and configured to maintain a circumferential length thereof. A plurality of fingers extend radially outwardly and generally axially from the base portion, a first set of the fingers extending generally in first axial direction, a second set of the fingers extending generally in a second axial direction opposite the first axial direction, such that the first and second sets of fingers extend toward each other to form a clamp-like structure.

Another aspect of the present invention relates to a heart valve prosthesis that includes a valve member that permits substantially unidirectional flow of fluid through the valve member. A support element generally is around at least a substantial part of a sidewall portion of the valve member to maintain a circumferential dimension thereof. A first set of substantially resilient fingers extend axially and radially outwardly from the first end of the support element. A second set of substantially resilient fingers extend axially and radially outwardly from the second end of the support element in a generally opposing relationship relative to the first set of fingers.

BRIEF DESCRIPTION OF THE DRAWINGS

FIG. 9 depicts an example of a heart valve prosthesis implanted at an aortic position in accordance with an aspect of the present invention.

FIG. 10 depicts an example of a heart valve prosthesis implanted at a pulmonic position in accordance with an aspect of the present invention.

DETAILED DESCRIPTION

Figure 1:
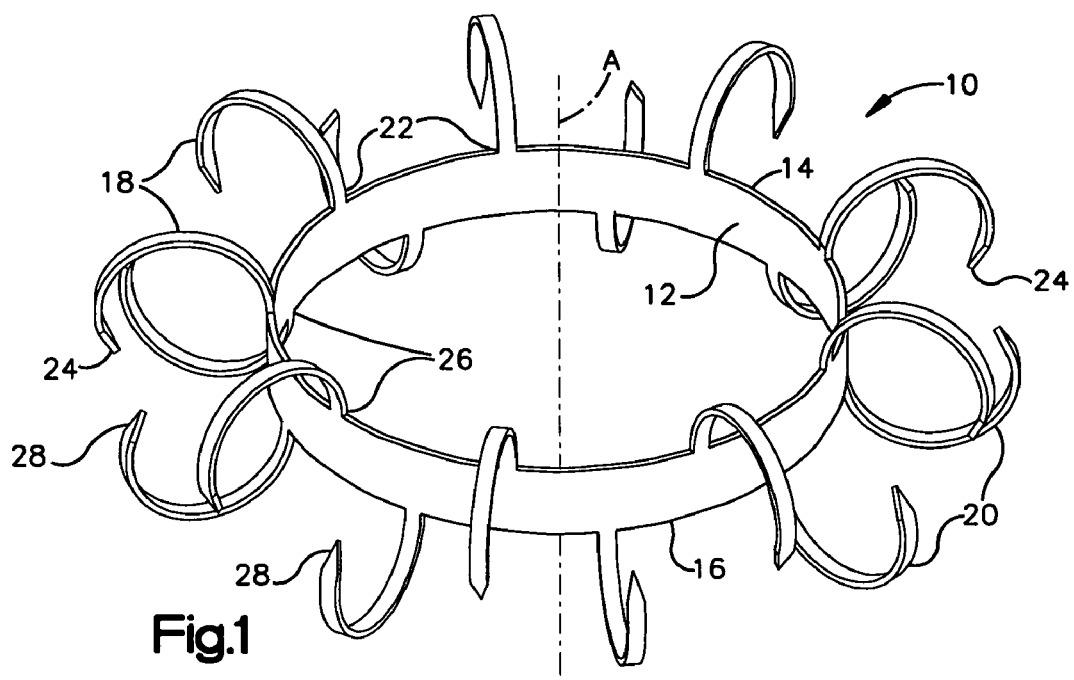
FIG. 1 depicts an example of a support apparatus in accordance with an aspect of the present invention.

FIG. 1 shows a support apparatus 10 in accordance with an aspect of the present invention. The support apparatus 10 includes an arcuate base portion 12. In the example of FIG. 1, the base portion 12 is in the form of a ring curved about an axis, indicated at A. The base portion has a sidewall portion extending axially between a first end 14 and a second end 16. As depicted in the example of FIG. 1, each of the ends 14 and 16 is substantially annular and continuous. The base portion 12, which extends between ends 14 and 16, can include a continuous (e.g. non-perforated) sidewall outer surface that extends axially between the first and second ends 14 and 16. The base portion 12 can be formed of a resilient to generally rigid material, such as metal or plastic. The base portion 12 is configured to maintain a circumferential dimension thereof. By maintaining a circumferential dimension, the periphery of the base portion 12 keeps a substantially constant length, even if the base portion is deformed. The base portion 12 can also be configured to have an adjustable axial length between the first and second ends 14 and 16.

A plurality of fingers 18 and 20 extend outwardly from the base portion 12. In the example of FIG. 1, the fingers include a first set of fingers 18 extending from the first end 14 and a second set of fingers 20 extending from the second end 16.

In the embodiment depicted in FIG. 1, each of the first set of fingers 18 is an elongate rod having a first end 22 attached to or integral with the base portion 12. An elongate body portion of each finger 18 extends arcuately radially outwardly and axially from the base portion 12 and terminates at a second end 24 that is spaced radially outwardly and generally co-planar with the base portion. Each of the second set of fingers 20 also can be an elongate rod having a first end 26 at the base portion 12. An elongate body portion of each finger 20 extends arcuately radially outwardly and axially from the base portion 12 to terminate at a second end 28. Thus, as shown in FIG. 1, the first and second sets of fingers 18 and 20 can be integral with the base portion 12 (i.e., the fingers and base portion can be monolithic, e.g., of single piece construction).

The respective sets of fingers 18 and 20 thus extend toward each other in substantially opposite directions so as to form a clamp-like structure, such as illustrated in FIG. 1. Additionally, the respective sets of fingers 18 and 20 can be arranged in a generally circular array circumferentially about the base portion 12. For example, each adjacent pairs of fingers 18 and 20 alternate in first and second axial directions with one another along the circumference of the base portion 12.

The second ends 24 and 28 can be sharpened to facilitate their insertion into tissue, such as at the annulus of a heart valve, as described herein. In this way, a heart valve incorporating the support apparatus can be implanted, without requiring sutures, and mitigate axially movement of the valve.

The fingers 18 and 20 can be constructed of a resilient material, such as a metal or plastic. A generally resilient material should be sufficient elastic to permit the fingers to be deformed from an original first condition (e.g., as shown in FIG. 1) to a second condition in which the sets of fingers 18 and 20 extend substantially linearly and generally parallel with the axis A (but in opposite directions relative to the base portion), and be capable of returning substantially to their original first condition.

In one particular example, the fingers 18 and 20, for example, can be formed of a shape memory alloy, such as a nickel-titanium alloy (e.g., nitinol). Shape memory (or thermal memory) is a characteristic in which a deformed part remembers and recovers to a pre-deformed shape upon heating. By forming the fingers 18 and 20 of a shape memory alloy, the fingers can be inelastically deformable to a new shape, such as substantially co-cylindrical with the annular base portion 12, when in its low-temperature (martensitic) form. When the fingers 18 and 20 are heated to a transformation temperature, which may vary according to the alloy composition, it quickly reverts to its high-temperature (austenitic) form, such as shown in FIG. 1. The base portion 12 can be formed of the same or a different material from that of the fingers 18 and 20. Those skilled in the art will appreciate various metals, plastics as well as other compositions or materials that can be utilized.

It should also be understood and appreciated by one skilled in the art that the pluralities of fingers 18 and 20 could take on a different configurations or dimensions according to different aspects of the present invention. For example, the fingers could be straight in the second condition, instead of curved, and have a sharpened hook, barb, or point at the end to make contact with the tissue of the annulus of the heart valve to anchor the heart valve prosthesis in place. Different thicknesses and widths could also be utilized.

Figure 2:
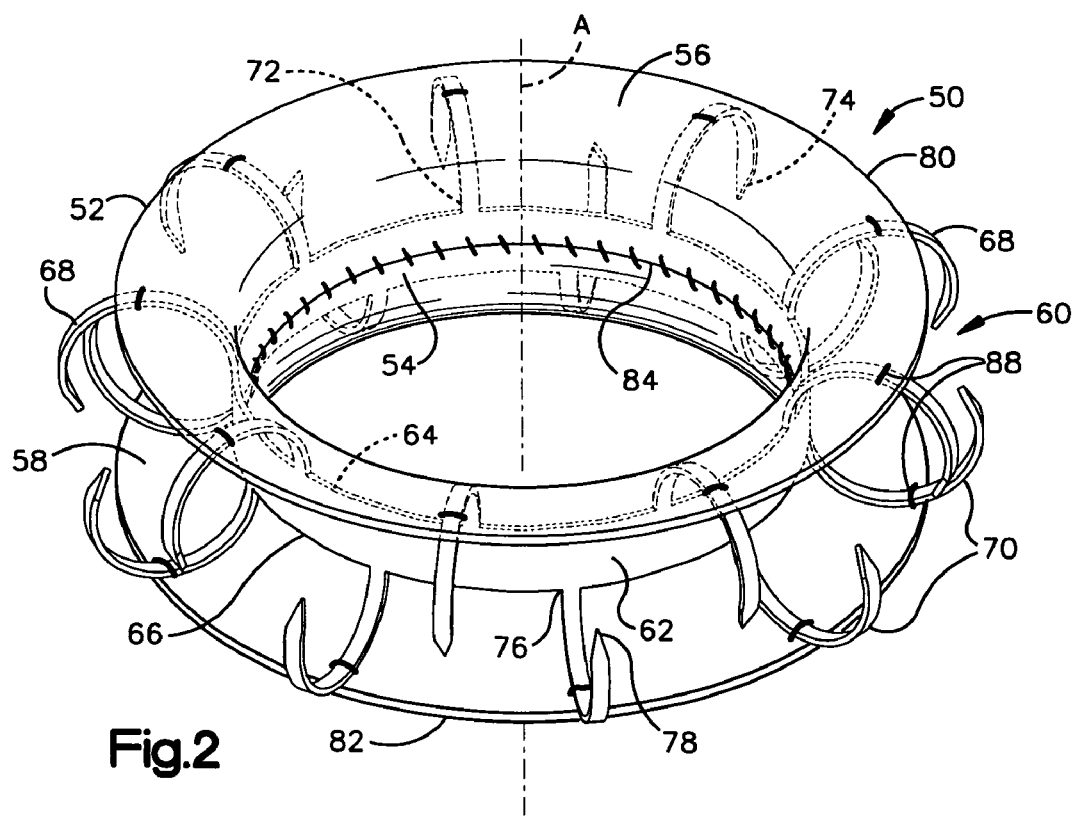
FIG. 2 depicts an example of the support apparatus of FIG. 1 with a covering in accordance with an aspect of the present invention.

FIG. 2 shows a covered support apparatus 50 in accordance with an aspect of the present invention. The covered support apparatus 50 includes a covering 52 and a support apparatus 60. The support apparatus can be substantially similar to that described with respect to FIG. 1. Briefly stated, the support apparatus 60 includes an arcuate base portion 62 curved about an axis A and having sidewall portion extending between first and second ends 64 and 66. A plurality of fingers 68 and 70 extend from the base portion, such as a first set of fingers 68 extending in a first generally axial direction, and a second set of fingers 70 extending in a second axial direction generally opposite that of the fingers 68. The respective sets of fingers 68 and 70 extend and curve toward each other to form a clamp-like structure, such as described herein.

Each finger 68 can be formed as an elongate rod extending between a first end 72 at the base portion 62 and a second end 74, which can be sharpened. Similarly, each finger 70 can be formed as an elongate rod extending between a first end 76 at the base portion 62 and a second end 78, which can also be sharpened. The respective fingers 68 and the 70 can be arranged circumferentially about the base portion 62 so that each adjacent pairs of fingers alternate between extending in first and second axial directions. The fingers 68 and 70 can be formed of a generally resilient material, such as metal or plastic. The covering 52 covers at least a portion of one or both sets of fingers 68 and 70. The covering 52 can be formed of one or more sheets of a biocompatible flexible material configured to cover at least a substantial part of an axially exposed surface of the respective sets of fingers 68 and 70. The covering 52 can also be operatively associated with the respective sets of fingers 68 and 70 so as to be moveable commensurate with movement of the fingers. The covering 52 mitigates exposure of the fingers to blood when implanted. Additionally, the covering can improve the sealing of the support apparatus when implanted.

In the example of FIG. 2, the covering 52 includes a tubular body portion 54 located within the base portion 62. Cover portions 56 and 58 extend from the tubular portion 54 to terminate in respective ends 80 and 82 to cover at least substantial part of an axially exposed surface of the respective sets of fingers 68 and 70. By way of further example, the covering 52 is formed of the a first cover portion 56 and the second cover portion 58, which are separated from one another by the generally tubular body portion 54 located within the base portion 62. That is, the base portion 62 circumscribes the tubular body portion 54 with the end portions 56 and 58 extending outwardly therefrom to cover the fingers 68 and 70, such as shown in FIG. 2. In one embodiment, the cover portions 56 and 58 can be formed of a pair of annular rings having substantially circular inner edges that are connected together, such as by sutures 84. The rings may be substantially identical in size and shape, although differently configured rings also could be used in accordance with the present invention. An outer portion of each of the rings thus forms the cover portions 56 and 58 that cover axially exposed portions of the respective fingers 68 and 70.

At least some of the fingers 68 can be connected to an adjacent cover portion 56 to enable movement of the cover portion as a function of movement of the respective fingers. Similarly, at least some of the fingers 70 can also be connected to the cover portion 58. In the example of FIG. 2, the fingers 68 and 70 are connected to respective cover portions 56 and 58 via sutures 88. Those skilled in the art will appreciate that other means for connecting the cover portion and fingers could be utilized. For instance, fingers could be inserted through the cover portion to provide a connection between the fingers and the cover portion. Alternatively or additionally, staples and/or adhesives could be employed to provide a suitable connection between the fingers and respective cover portions. Those skilled in the art will appreciate that, while a single suture is depicted to connect each finger with the cover portion, more than one suture could be used.

The connection between the plurality of fingers 68 and 70 and the respective cover portions 56 and 58 allows the cover portions to be moveable with relation to the movement of the pluralities of fingers 68 and 70 and continue to cover the fingers throughout their movement.

The biocompatible flexible material covering 52 could be any flexible tissue (natural or synthetic) material. In one embodiment, the covering 52 is formed from one or more sheets of a biological tissue material, such as animal pericardium (e.g., bovine, equine, porcine, human, etc.), dura matter, collagen, and the like. The biological tissue material may be chemically treated in a suitable fixation solution, such as including glutaraldehyde. By way of further illustration, the covering 52 (including cover portions 56 and 58) may be formed from a NO-REACT® tissue product, which is commercially available from Shelhigh, Inc., of Millburn, N.J. The NO-REACT® tissue products help improve the biocompatibility of the apparatus 50, thereby mitigating the likelihood of a patient rejecting an implanted prosthesis that includes the apparatus. The NO-REACT® tissue also resists calcification when implanted. Those skilled in the art will appreciate various other materials that could be utilized for the covering 52, including as cloth (e.g., Dacron) as well as other biocompatible materials (natural or synthetic).

While FIG. 2 illustrates the covering 52 as formed from two separate cover portions 56 and 58, it will be appreciated by one skilled in the art that any number of one or more sheets could be utilized to form the covering. For instance, an individual covering could be associated with each of the fingers (e.g., in the form of a coating or tab).

When implanted, such as described herein, the biocompatible covering 52 helps shield the fingers 68 and 70 from the blood that passes through the heart valve prosthesis. For instance, as the pluralities of fingers 68 and 70 penetrate the tissue at an implantation site (e.g., at the annulus of a heart valve), the covering 52 can also form a seal around the annulus, helping to conceal the support apparatus 50 from contact with blood. As a result, possible clotting or other negative side effects may be mitigated.

Figure 3:
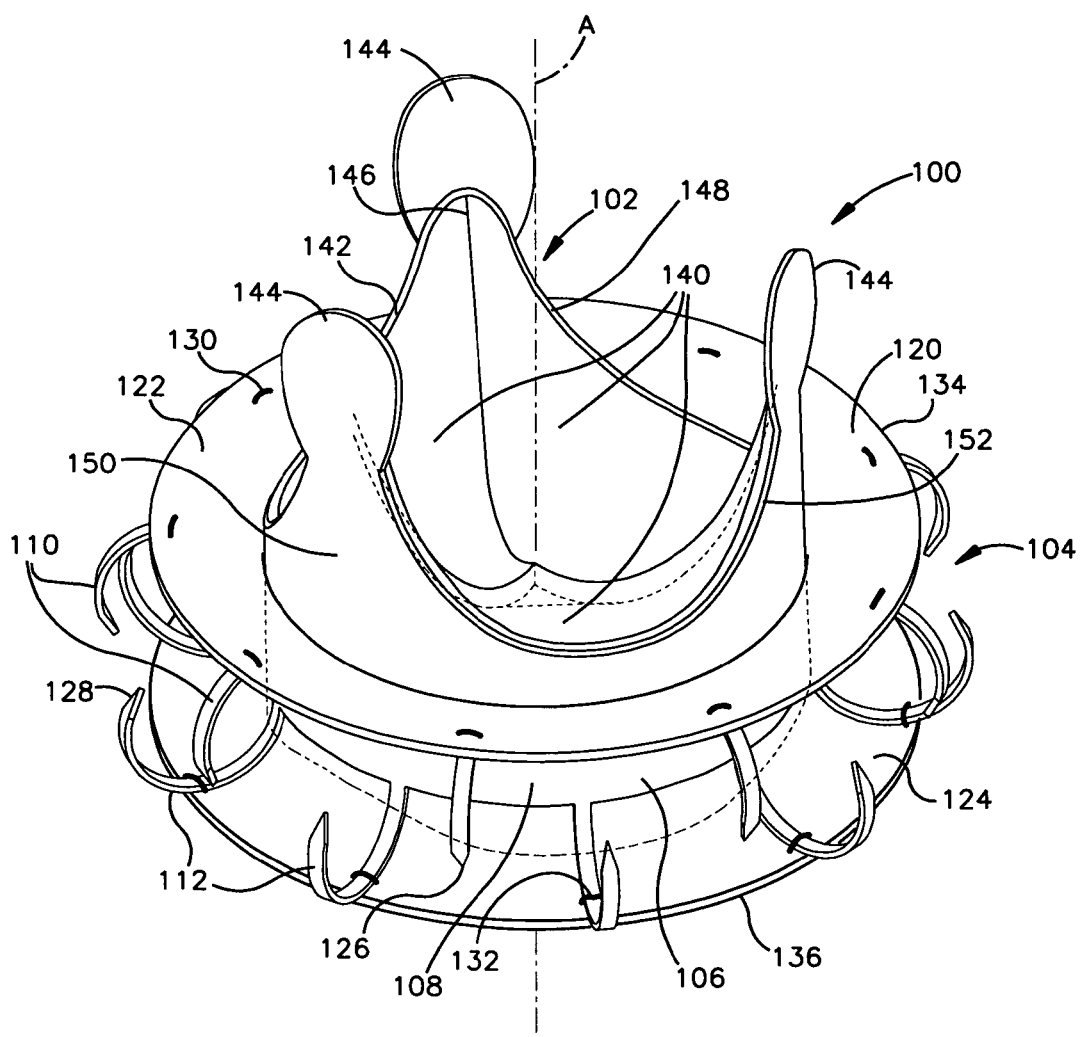
FIG. 3 depicts an example of a heart valve prosthesis in accordance with an aspect of the present invention.

FIG. 3 depicts a heart valve prosthesis 100 that can be implemented in accordance with an aspect of the present invention. The prosthesis 100 includes heart valve 102 located within a covered support apparatus 104. The inner diameter of the covered support apparatus 104 approximates the outer diameter of the heart valve 102. The heart valve 102 can be mounted to the covered support apparatus 104, such as by sutures or other connecting means.

The covered support apparatus 104 can be substantially similar to that shown and described with respect to FIG. 2. Briefly stated, the covered support apparatus 104 includes a support member 106 having an arcuate base portion 108 curved about an axis A. The base portion 108 may be a complete ring that substantially circumscribes the heart valve 102. The base portion 108 helps to maintain a circumferential dimension (e.g., peripheral length) of an annulus of the heart valve 102. A first plurality of fingers 110 and a second plurality of fingers 112 extend from the base portion 108. The plurality of fingers 110 extend in a first generally axial and radially outward direction. The other plurality of fingers 112 extend in a second generally axial and radially outward direction. The pluralities of fingers 110 and 112, respectively, extend and curve toward each other, such that the respective sets of fingers cooperate to form a generally clamp-like structure.

The covered support apparatus 104 also includes at least one covering 120 configured to cover at least some of the fingers 110 and 112. In the example of FIG. 3, the covering 120 includes an outflow portion 122 and an inflow portion 124. A tubular body portion (not shown, see FIG. 2) can connect the respective inflow and outflow portions.

Each finger in the plurality of fingers 110 and 112 can extend arcuately from the base portion and terminate in a sharpened end 126 and 128, respectively, spaced outwardly from the base portion 108. These sharpened ends 126 and 128 facilitate penetration into the tissue of at the implantation site of the patient, thus helping to anchor the heart valve prosthesis.

The respective sets of fingers 110 and 112 are arranged in a generally circular array extending from the base portion 108 so that adjacent pairs of fingers alternate in first and second axial directions with one another along the circumference of the base portion 108.

The covering 120 can be connected for movement with one or both of the pluralities of fingers 110 and 112. For example, the outflow and inflow portions 122 and 124 can be connected to some or all of the respective fingers 110 and 112, such as by sutures 130 and 132. For instance, a radially outer end 134 of the outflow cover portion 122 can be sutured to an intermediate portion of at least some of the fingers 110 along the length of such fingers. Similarly, a radially outer end 136 of the inflow cover portion 124 can be sutured to an intermediate portion of at least some of the fingers 112 along the length of such fingers. The connection between to the plurality of fingers 110 and 112 and the covering 120 allows the covering to be moveable with relation to the movement of the pluralities of fingers and continue to cover them throughout their movement.

The fingers 110 and 112 can be constructed of a resilient material, such as a metal or plastic. This resilient material, for example, can be a shape memory alloy, such as nitinol. This material allows the fingers 110 and 112 to move from a second condition, in which the distal ends 126 and 128 of the fingers are spaced apart and generally co-cylindrical with the base portion 112, back to a first original condition, in which the fingers form a clamp-like structure, such as shown in FIG. 3.

The heart valve 102 is depicted as a biological heart valve, although those skilled in the art will appreciate that any type of heart valve, including a biological tissue valve, a mechanical valve, or a hybrid bio-mechanical valve (e.g., part mechanical and part biological tissue), could be utilized. The heart valve 102 includes one or more (e.g., three in the example of FIG. 3) leaflets 140 mounted within a sidewall portion 142. For example, the valve 102 can be a natural heart valve harvested from an animal (e.g., pig, horse, cow, human, etc.), such that the sidewall portion corresponds to the associated valve wall harvested from the animal. Alternatively, the valve 102 can be manufactured from biological material, such that at least part of the valve includes biological tissue material. The heart valve 102 can be stented or unstented.

An outflow lobe (or extension) 144 is located at an outflow end 148 of the valve 102 near each of one or more commissures 146. The lobes 144 extend a predetermined distance beyond and lateral to each of the commissures 146 at the outflow end 148 of the valve 102. The surgeon implanting the prosthesis 100 may thus cut the lobes 144 to a desired shape and size. The particular size of the lobes 144 also will depend upon the size of the prosthesis 100. Intermediate each adjacent pair of lobes 144, the outflow end 152 of the sheath 150 can follow the contour of the outflow end 148 of the valve 102 (e.g., generally sinusoidal outflow end).

The lobes 144 can be part of an outer sheath 150 that surrounds the valve 102, as depicted in FIG. 3. Alternatively, the lobes 144 can be sheets of tissue (e.g., natural or synthetic) attached at the outflow end 148 at the commissures 146 of the valve 102. The lobes 144 thus provide extensions at the outflow end commissures 146, which can be secured to a patient's tissue (e.g., the patient's valve wall). By securing the lobes 144 of an implanted prosthesis 100 to surrounding tissue, respective commissures 146 can be generally fixed to the surrounding tissue to mitigate prolapse as well as to help ensure proper coaptation between the leaflets 140.

The sheath 150 includes an inflow end portion (not shown) and an outflow end portion 152, a portion of which extends beyond the commissures 146 of the valve 102 to form the lobes 144. In the example of FIG. 3, the sheath 150 can be formed of a biological tissue material, such as porcine or equine pericardium that has been appropriately fixed in a glutaraldehyde solution and detoxified (e.g., similar to the NO-REACT® tissue described above). The sheath 150 can be attached to valve 102 as part of such fixation and detoxification processes.

Figure 4:
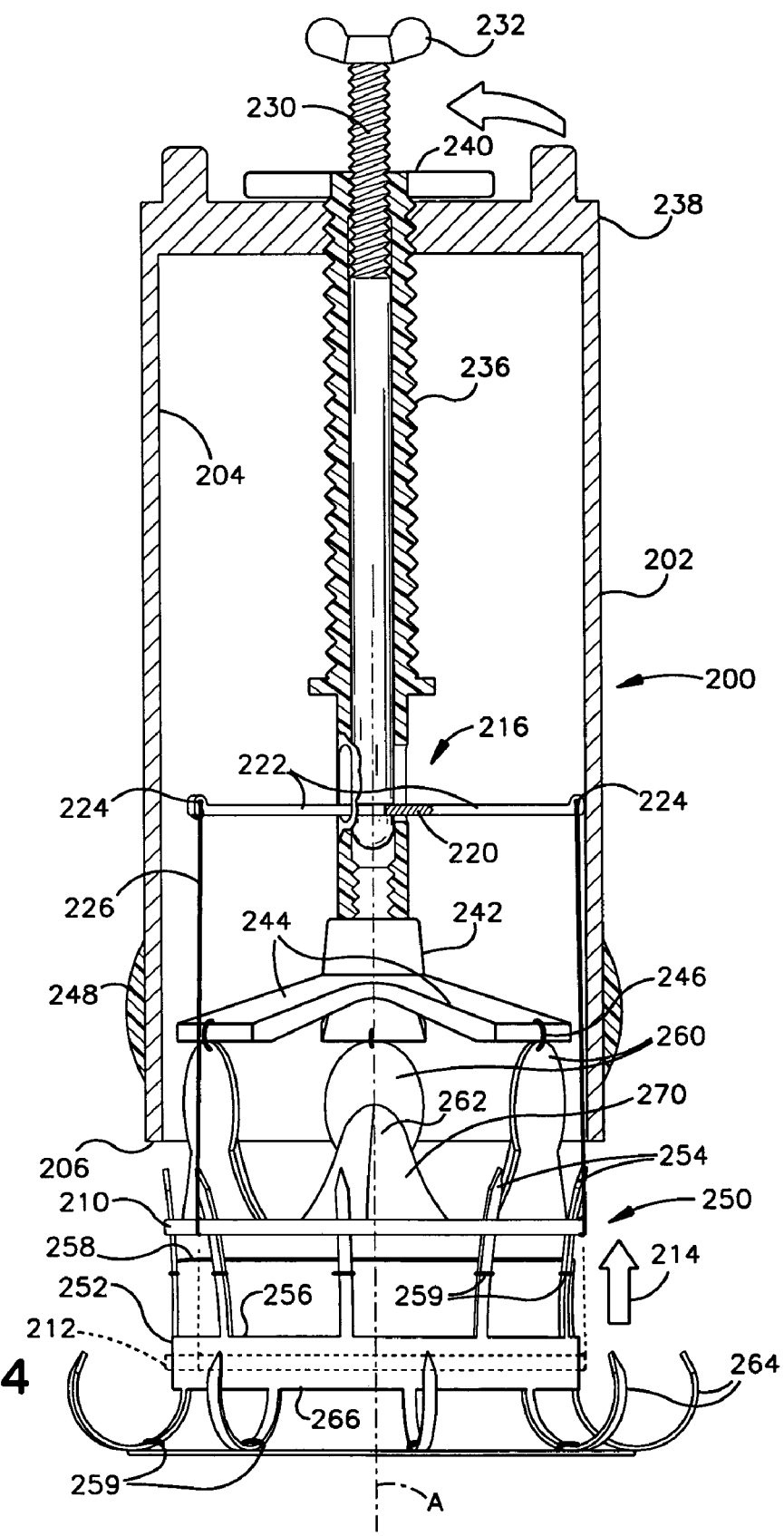
FIG. 4 depicts an example of a heart valve prosthesis being loaded into an implanter in accordance with an aspect of the present invention.
Figure 5:
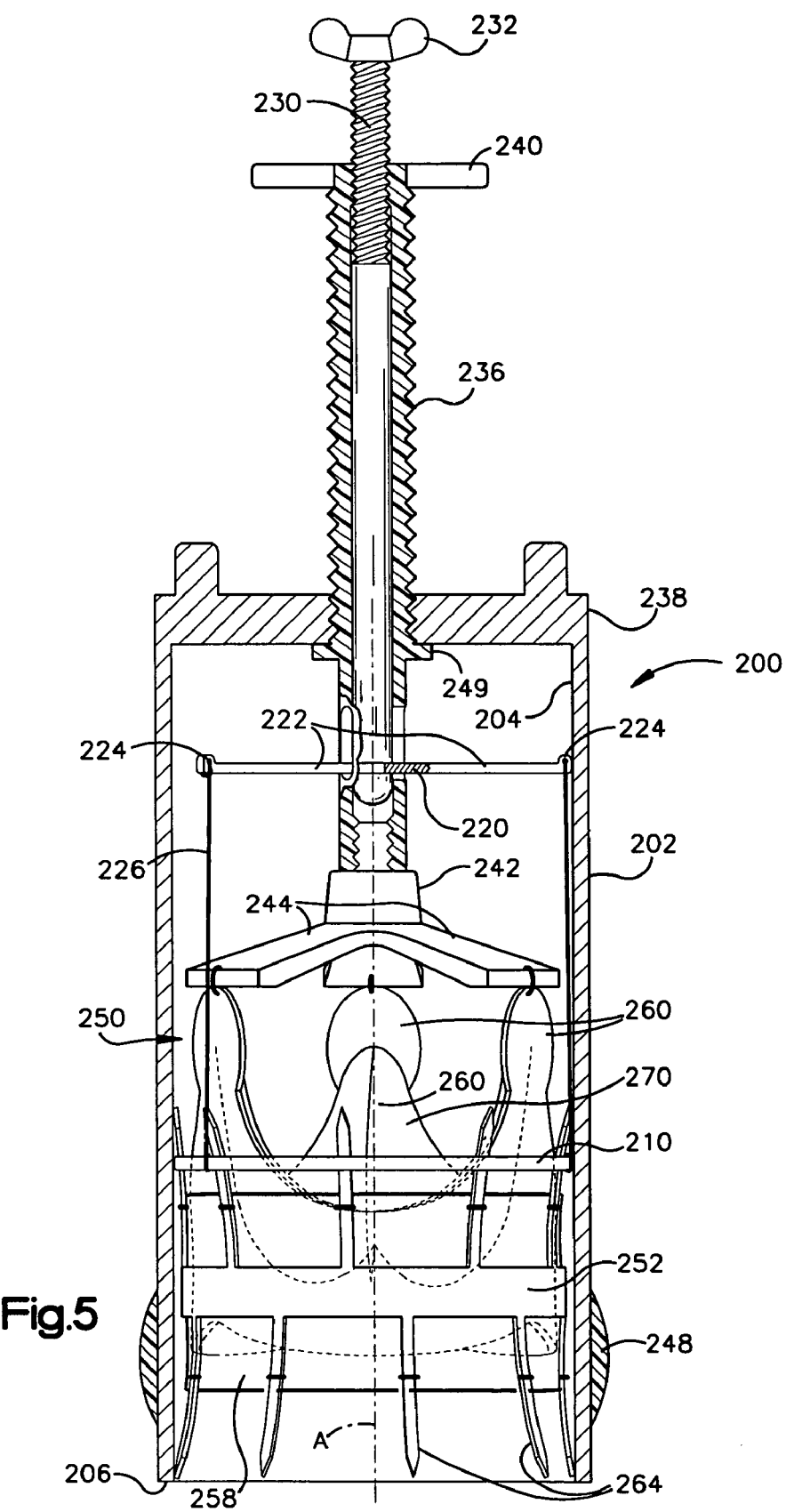
FIG. 5 depicts an example of a heart valve prosthesis loaded into an implanter in accordance with an aspect of the present invention.
Figure 6:
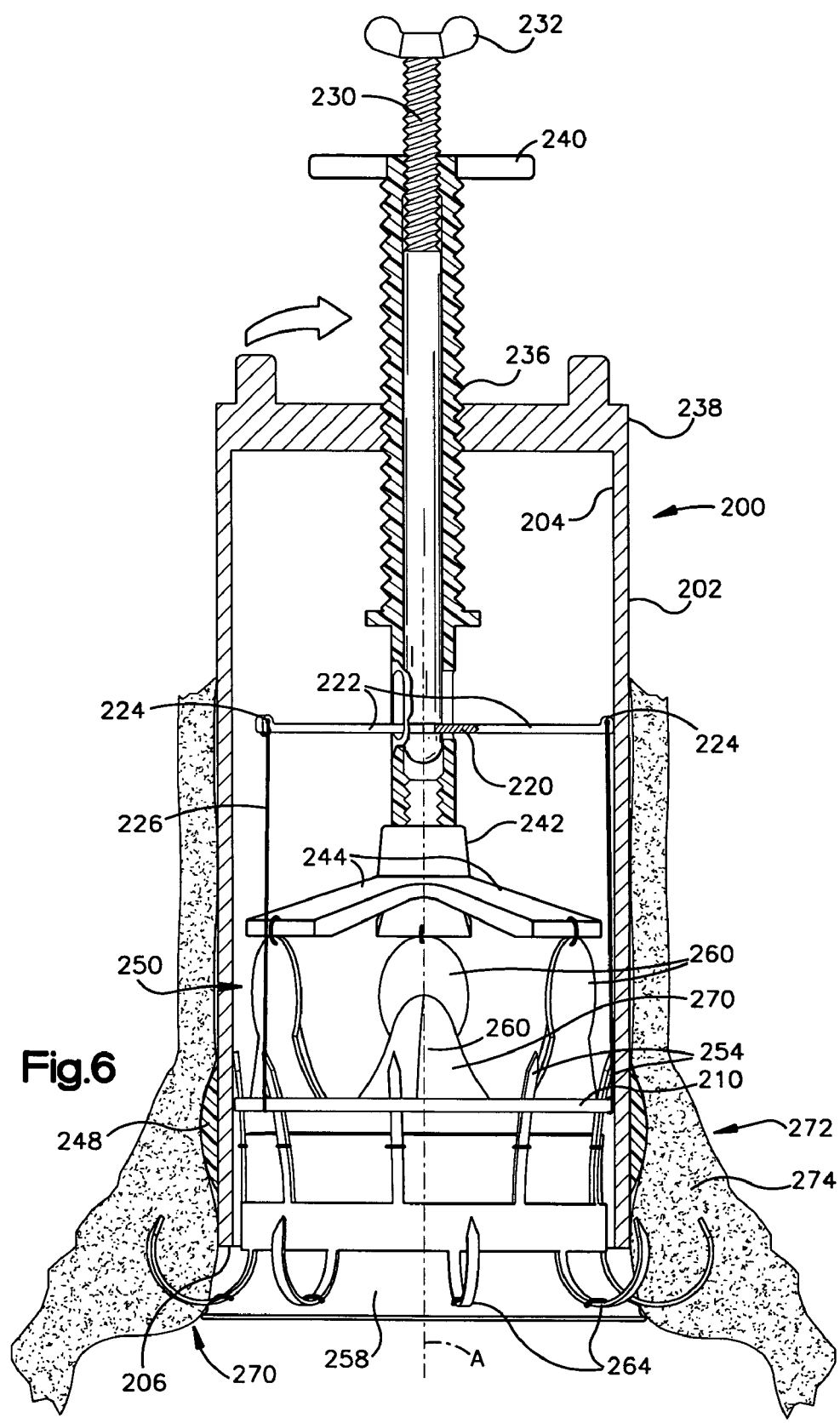
FIG. 6 depicts an example of a heart valve prosthesis being implanted in tissue in accordance with an aspect of the present invention.
Figure 7:
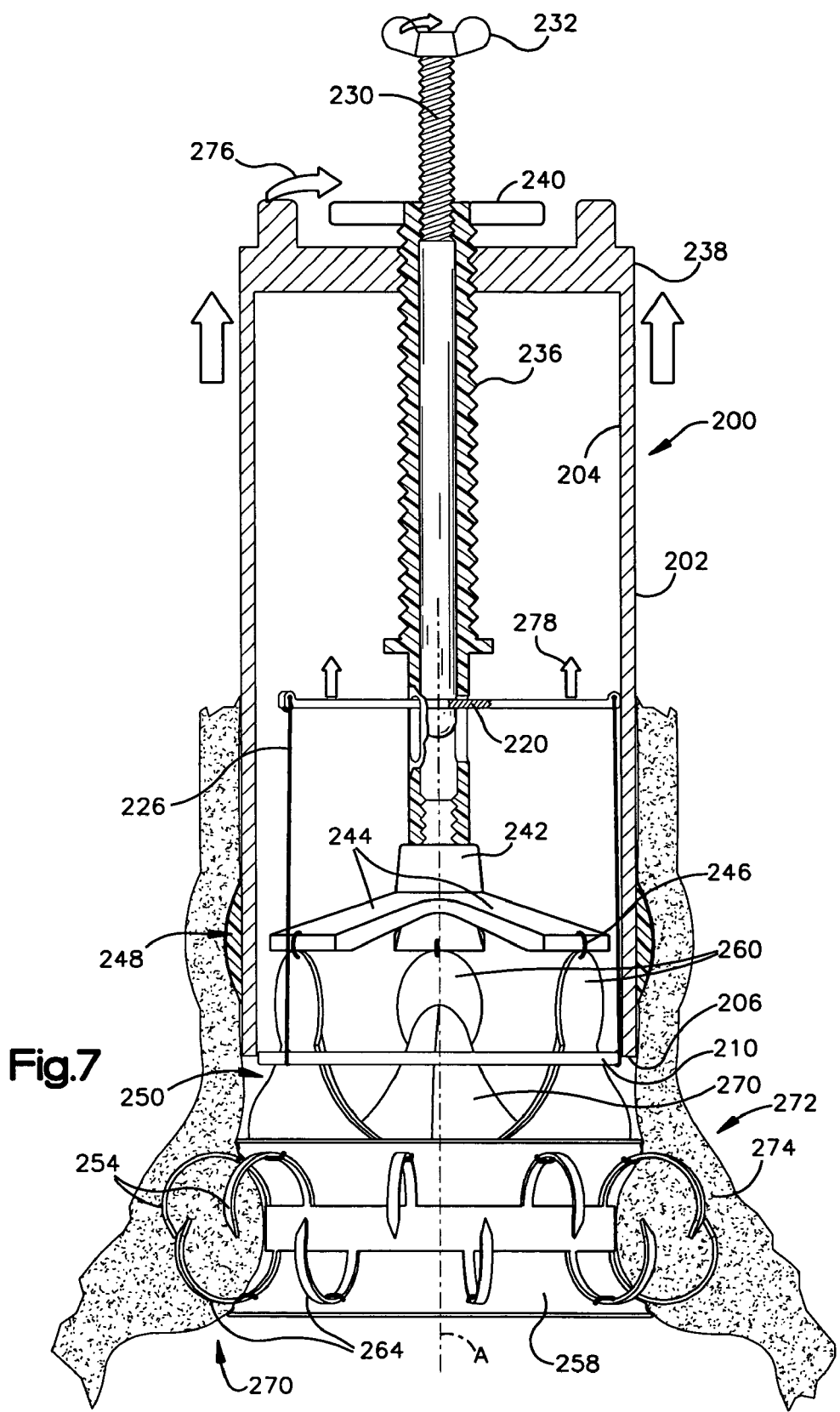
FIG. 7 depicts another example of the heart valve prosthesis of FIG. 6 being implanted in tissue in accordance with an aspect of the present invention.

FIGS. 4, 5, 6 and 7 depict a partial sectional view of an implanter device 200 in combination with a heart valve prosthesis 250 according to an aspect of the present invention. FIGS. 4 and 5 demonstrate but one example approach that can be employed to install the heart valve prosthesis 250 in the implanter 200, while FIGS. 6 and 7 depict an example of using the implanter 200 to implant the prosthesis at a desired implantation site. Identical reference numbers are used to refer to the common elements depicted in FIGS. 4, 5, 6 and 7. Additionally, the heart valve prosthesis 250 depicted in FIGS. 4, 5, 6 and 7 can be substantially similar to that described above in FIG. 3, although other types of valves can also be utilized with the implanter 200. Additionally, those skilled in the art may understand and appreciate other types of implanters that can be utilized with a heart valve prosthesis implemented in accordance with an aspect of the present invention.

The implanter device 200 includes a cylindrical member 202 with an interior wall 204 that has a dimension that approximates (e.g., is slightly greater than) an outer dimension of a base portion 252 of the prosthesis 250. The implanter device 200 also comprises an open distal end 206 at one end of the cylindrical member. The interior dimension of the cylindrical member 202 (at least near the distal end 206) is dimensioned and configured for receiving the prosthesis 250 therein.

In order to facilitate loading the prosthesis 250 into the implanter 200, a retaining mechanism 210 can be associated with the implanter. The retaining mechanism 210 can be in the form of a retaining ring dimensioned and configured to slide along the exterior of the prosthesis 250. For example, the retaining mechanism 210 initially is located at a first position, indicated at dotted line 212, in which it generally circumscribes the base portion 252 of the prosthesis 250. The retaining mechanism 210 can then be urged axially in the direction of arrow 214 to a second position (indicated in solid line) to reposition a plurality of fingers 254 from an original first position to the second position, as depicted in FIG. 4. The plurality of fingers 254 extend generally from a first end 256 of the base portion 252. A covering 258 of a biocompatible material is connected for movement with the fingers 254, such as by sutures 259. By moving retaining mechanism to the second position, the fingers 254 are thus oriented to extend generally parallel (e.g., co-cylindrical) with the sidewall of the base portion 252. The covering 258 also moves as a function of the motion of the fingers 254. As a result, the inflow end of the prosthesis 250 can be urged into the distal end 206 of the implanter 200.

In the example of FIG. 4, the implanter includes a guide system 216 operative to move the retaining mechanism 210 for repositioning the fingers 254 to the second position. The guide system 216 includes a hub 220 located internally to the cylindrical member 202. The hub 220 comprises an array of spokes 222 that extend radially outward from the hub. A radial outer end of the respective spokes 222 provides an eyelet or aperture 224. A number of connecting elements (e.g., sutures) 226 connect each eyelet 224 to the retaining mechanism 210, so that the retaining mechanism moves commensurately with axial movement of the hub 220 and spoke 222 assembly.

An inner threaded member 230 is coupled to the cylindrical member 202 to control the axial position of the hub 220 and spoke 222 assembly within the cylindrical member. An upper handle or knob member 232 is fixed to the inner threaded member 230 to facilitate its rotation about an elongate axis. Thus, rotating the handle 232 to cause rotation of the inner threaded member 230 provides for corresponding axial movement of the hub 220 and spoke 222 assembly. This can provide for corresponding movement of the retaining ring 210 in the direction 214, such as to move the retaining ring from the position 212 to the second position. By moving the retaining mechanism 210 to the second position, the fingers 254 are urged in the direction 214 so as to provide an outer diameter that allows the heart valve prosthesis 250 to be installed within the cylindrical member 202.

The heart valve prosthesis 250 is connected for movement relative to the cylindrical member 202 to enable installation and discharge of the prosthesis to and from the cylindrical member. In the example of FIGS. 4 and 5, an outer threaded member 236 is threaded for axial movement relative to a proximal end 238 of the cylindrical member 202. The inner threaded member 230 is counter-threaded within the outer threaded member 236. The outer threaded member 236 can be rotated by manipulation of an associated handle member 240 to control the axial position of the outer threaded member.

A guide structure 242 is attached at a distal end of the outer threaded member 236 and, thus moves axially commensurate with axial movement of the outer threaded member. The guide structure is attached to the heart valve prosthesis 250. For example, the guide structure 242 includes a plurality of arms 244 that extend from a central part of the guide structure. Each of the arms 244 can be attached to an outflow end of the heart valve prosthesis 250, such as by sutures 246. For instance, the sutures 246 can connect the arms 244 with axially extending lobes 260 at the outflow end of the lobes extending from near commissures 262 of the valve 270. Alternatively, if the lobes 260 are not implemented in the prosthesis 250, the arms 244 could be connected to any other suitable outflow structure.

The number of arms 244 can correspond to the number of lobes 260 on the heart valve prosthesis 250, although other configurations can also be utilized depending on the configuration of heart valve prosthesis 250. These connections of the lobes 260 to the guide structure arms 244 hold the heart valve prosthesis 250 in place and help guide the heart valve prosthesis 250 into and out of the distal end 206 of the implanter device 200. It will be understood and appreciated by one skilled in the art that means can be employed to connect the arms 244 to the lobes 260 other than the sutures 246, as depicted in FIGS. 4 and 5.

On the outside of the cylindrical member 202, there is a bulbous portion 248 that surrounds at least part of the outer circumference of the cylindrical member 202. This bulbous portion 248 is located proximal the distal end 206 of the cylindrical member 202. The bulbous portion 248 can be integral with the cylindrical member 202 or, alternatively, it can be a separate cylindrical member that may be adjustably mounted along the exterior of the sidewall member. The bulbous portion 248 provides a means for inhibiting insertion of the distal end 206 of the implanter 200 relative to an annulus more than a predetermined amount. For instance, the bulbous portion 248 can inhibit insertion of the cylindrical member beyond a predetermined distance from the implantation site (e.g., annulus). As a result, the distal end 206 of the cylindrical member 202 can be efficiently and accurately placed so as to facilitate positioning the prosthesis 250 for implantation at the desired implantation position.

In the example of FIG. 4, the first plurality of fingers 254 are positioned for insertion into the cylindrical member 202, as the fingers 254 have been moved to have a cross-sectional dimension that approximates or is less than an internal diameter of the cylindrical member 202 at the distal end 206. As described herein, the fingers 254 are biased or otherwise capable of returning to their original configuration. A second plurality of fingers 264 extend from an inflow end 266 of the base portion 252. The fingers are attached to another part of the covering 258 (e.g., by sutures 259). In the example of FIG. 4, the second plurality of fingers 264 extend arcuately from the base portion 252, radially outwardly and axially.

FIG. 4 thus shows a first phase for loading or inserting the heart valve prosthesis 250 into the implanter 200, such as can be done prior to surgical implantation. As mentioned above, by rotating the upper handle member 232, the inner threaded member 230 rotates, causing the hub 220 and spoke 222 assembly to move axially in the direction 214 so as to pull the sutures 226 and the retaining mechanism 210 axially relative to the heart valve prosthesis 250. This results in urging the plurality of fingers 254 from the first condition of a curved half-clamp to the condition shown in FIG. 4.

Once the finger retaining mechanism 210 is in the second condition, as shown in FIG. 4, the lower handle member 240 is rotated, causing the outer threaded member 236 to rotate. This causes relative rotation of the cylindrical member 202 and the heart valve prosthesis 250, which, in turn, provides for axial movement of the prosthesis 250. In this way, the heart valve prosthesis 250 can be loaded into the implanter device 200. As the heart valve prosthesis 250 is moved into the cylindrical member 202 beyond the base portion 252, the distal end 206 of the cylindrical member engages the second plurality of fingers 264 to urge the fingers to a generally parallel position relative to the base portion 206.

FIG. 5 illustrates the implanter device 200 containing a heart valve prosthesis 250 completely loaded within the cylindrical member 202. The inner sidewall 204 of the cylindrical member 202 engages the second plurality of fingers 264. A stop feature 249 can extend outwardly from the outer threaded member 236 to engage the inside of the proximal end 238 of the cylindrical member to control the length that the threaded member can be threaded through the proximal end.

It is to be appreciated that after the prosthesis 250 has been loaded into the cylindrical member 202, the retaining mechanism can be removed from the first plurality of fingers 254, such that the fingers engage the inner sidewall 204 similar to the other fingers 264.

As mentioned above, FIGS. 6 and 7 depict the implanter 200 in connection with a process for implanting the heart valve prosthesis 250, such as at an annulus 270 of an implantation site 272. For example, the implantation site can correspond to an aortic annulus (e.g., to replace an aortic valve) or, alternatively, to a pulmonic annulus (e.g., to replace a pulmonic valve). In the illustration of FIG. 6, the cylindrical member 202 of the implanter 200 has been inserted to position the distal end 206 of the cylindrical member 202 at the annulus 270. The bulbous portion 248 has collided with the annulus 270, thereby indicating to the implanting surgeon that the implantation device 200 has been position at the proper location for the implantation procedure.

In the illustration of FIG. 6, the second plurality of fingers 264 has already emerged from within the cylindrical member 202 such that the fingers have returned to their original configuration. The return of the fingers to their original shape is a result of discharging the prosthesis 250 from the implanter 200. The prosthesis can be discharged from the implanter in a controller manner in response to rotation of the lower handle member 240 (e.g., in a counter-clockwise direction) relative to the cylindrical member 202. Thus, as the fingers 264 are urged from the distal end 206, they return to their original shape so as to penetrate into tissue 274 at the annulus 270, such as depicted in FIG. 6. The penetration of the fingers 264 anchors the heart valve prosthesis 250 to inhibit axial motion in the direction of blood flow through the annulus 270. The attachment of the plurality of fingers 264 to the biocompatible flexible material covering 258 allows the biocompatible flexible material cover 258 to follow the movement of the plurality of fingers 264. As a result, the covering 258 thus is urged radially outwardly so as to engage an inner sidewall of the annular 270, as shown in FIG. 6.

FIG. 7 shows a continuation of the implantation procedure shown in FIG. 6. In FIG. 7, the heart valve prosthesis 250 has been discharged from the implanter 200 to such an extent that the other set of fingers 254 has been discharged from the distal end 206 and released from the retaining mechanism 210. As result, the fingers 254 return to their original position so as to penetrate the surrounding tissue 274 at the annulus 270. The attachment of the plurality of fingers 254 to the biocompatible flexible material cover 258 further allows the biocompatible flexible material covering to follow the movement of the plurality of fingers 254. The plurality of fingers 254, having dug into the tissue around the annulus of the heart, anchors the heart valve prosthesis 250 and prevents it from axial movement in the direction opposite the flow of blood through the annulus. Thus, the first and second sets of fingers 254 and 264 cooperate to inhibit axial as well as rotation movement of the prosthesis relative to the annulus 270 of the implantation site 272.

The movement of the cylindrical member 202 relative to the heart valve prosthesis 250 can be implemented by rotation of the outer threaded member counter-clockwise, as indicated by arrow 276. Additionally, the retaining mechanism 210 can be moved in the direction of arrow 278 to release the fingers 254, such as by rotation of the upper handle member 232 relative to outer threaded member 236. Such relative rotation between the threaded members 230 and 236 causes the hub 220 and spoke 222 assembly attached thereto to move independent of the cylindrical member 202. It will be appreciated that the retaining mechanism 210 can be moved to release the fingers 254 at substantially any time after the fingers 254 have been positioned within the cylindrical member.

After both sets of fingers 254 and 264 have penetrated into the tissue 274, the biocompatible flexible material covering 258 serves to mitigate exposure of the fingers 254 and 264 to blood. The biocompatible flexible material covering 258 also provides a seal around the annulus 270, concealing the non-biocompatible materials from contacting blood as it flows through the annulus. This further helps prevent the blood from possible clotting or any other negative side effects that might occur.

After both pluralities of fingers 254 and 264 have penetrated into the tissue, as depicted in FIG. 7, the cylindrical member 202 can continue to be moved axially away from the heart valve prosthesis 250. Such movement can be achieved by rotating the lower handle member 240, which causes the outer threaded member 236 to rotate accordingly. Once the heart valve prosthesis 250 has been discharged from the implanter device 200, the sutures 246 that attach the guide arms 244 to the lobes 260 of the heart valve prosthesis 250 can be removed. The implanter can then also be removed from the implantation site 272.

Figure 8:
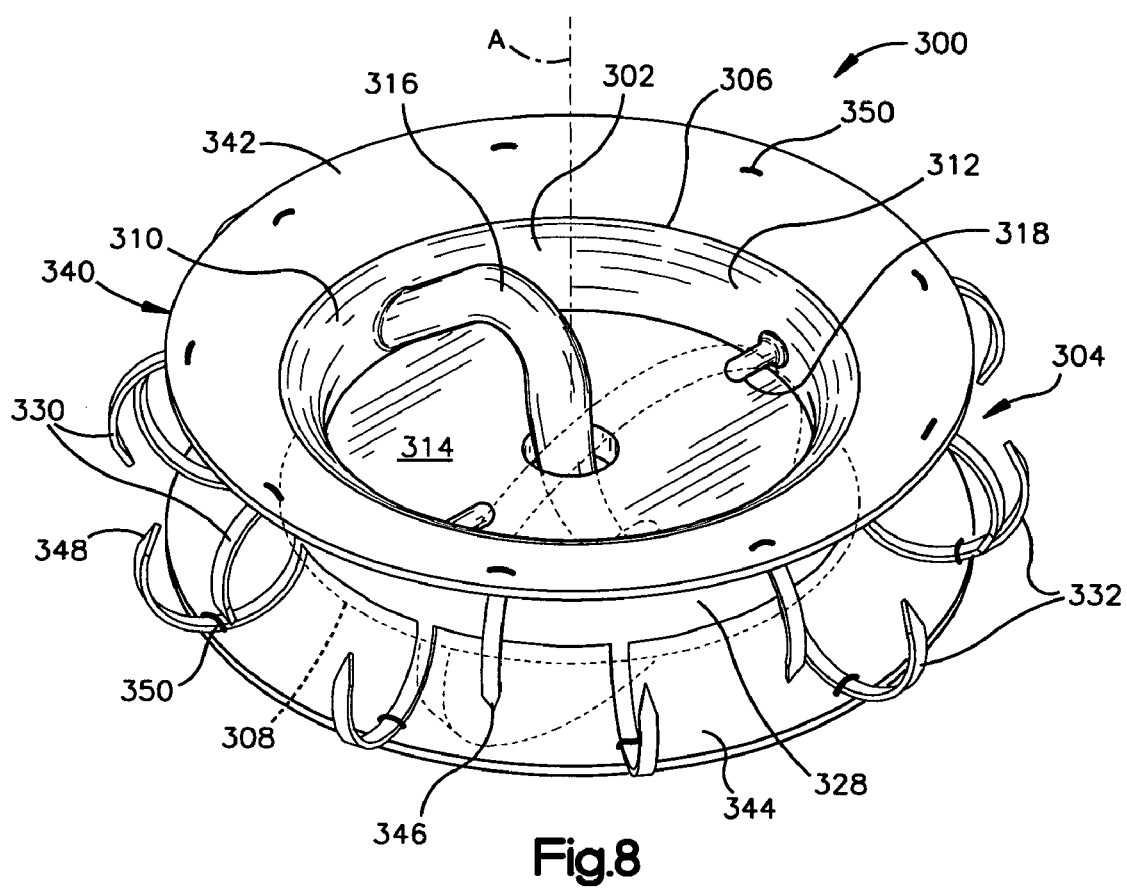
FIG. 8 depicts an example of a mechanical heart valve prosthesis in accordance with an aspect of the present invention.

FIG. 8 illustrates a mechanical heart valve prosthesis 300 that can be implemented in accordance with another aspect of the present invention. The prosthesis includes a mechanical heart valve 302 mounted generally coaxially within a covered support apparatus 304 in accordance with an aspect of the present invention. The mechanical heart valve 302 has an inflow end 306 and an outflow end 308 to define a substantially unidirectional flow of blood through the valve.

The heart valve 302 includes a generally annular base portion or annulus 306. In the example FIG. 8, the annulus 310 includes a generally cylindrical portion 312 that extends axially between spaced apart end portions 306 and 308. The end portions 306 and 308 further define flange portions that extend radially outwardly relative to the intermediate cylindrical portion. The flange portions at the ends 306 and 308 help retain the support apparatus at a desired axial position between the ends when positioned around the valve 302.

The valve 302 also includes a valve portion 314 that is moveable between open and closed conditions to permit substantially unidirectional flow of blood through the valve. The valve portion 314 is illustrated as a generally circular disk mounted to the annulus 306 by a pivot arm 316 extending between a central part of the valve 302 and an inner sidewall of the annulus 310. The valve portion 314 is moveable along the pivot arm 316 and engages pivot elements 318 to provide for desired rotation of the valve portion 314 within the annulus 306 to provide corresponding open and closed conditions.

Those skilled in the art will understand and appreciate that other types of mechanical or bio-mechanical heart valves can be utilized to provide a prosthesis in accordance with an aspect of the present invention. Examples of mechanical heart valves that may be utilized in accordance with an aspect of the present invention are commercially available from various vendors, including Medtronic, Inc.; Omniscience, Inc.; St. Jude Medical; and others.

The covered support apparatus 304 can be substantially similar to that shown and described with respect to FIG. 2, with the base portion dimensioned and configured to surround the annulus 306 of the mechanical valve 302. Briefly stated, the covered support apparatus 304 includes a support member having an arcuate base portion 328 curved about an axis A. The base portion 328 may be a complete ring that substantially circumscribes the heart valve 302 or it can be a generally C-shaped support. A first plurality of fingers 330 and a second plurality of fingers 332 extend from the base portion 328. The plurality of fingers 330 extend in a first generally axial and radially outward direction relative to the base portion 328. The other plurality of fingers 332 extend in a second generally axial and radially outward direction substantially opposite the first set of fingers 330. The respective pluralities of fingers 330 and 332, respectively, extend and curve toward each other, such that the respective sets of fingers cooperate to form a generally clamp-like structure.

The covered support apparatus 304 also includes at least one covering 340 configured to cover at least some of the fingers 330 and 332. In the example of FIG. 8, the covering 340 includes first and second portions 342 and 344 that cover at least substantial portions of the respective fingers 330 and 332. A tubular body portion (not shown, see FIG. 2) can connect the respective inflow and outflow portions and surround the annulus 306 of the valve 302.

Each finger in the plurality of fingers 330 and 332 can extend arcuately from the base portion and terminate in a sharpened end 346 and 348, respectively, spaced outwardly from the base portion 328. These sharpened ends 346 and 348 can penetrate into tissue at the implantation site of the patient, as described herein, to help anchor the heart valve prosthesis 300.

The respective sets of fingers 330 and 332 are arranged in a generally circular array extending from the base portion 328 such that adjacent pairs of fingers alternate between extending in first and second axial directions with one another along the circumference of the base portion 328. The fingers 330 and 332 can be constructed of a resilient material, such as described herein.

The covering 340 can be connected for movement with one or both of the plurality of fingers 330 and 332. For example, the covering portions 342 and 344 can be connected to some or all of the respective fingers 330 and 332, such as by sutures 350. The connection between the plurality of fingers 330 and 332 and the covering 340 allows the covering to be moveable with relation to the motion of the fingers 330 and 332 and continue to cover the fingers throughout their movement. The covering 340 can be formed of a flexible biocompatible material, such as one or more sheets of a natural or synthetic material, as described herein.

FIG. 9 illustrates an example of a heart valve prosthesis 400 implanted in a heart 402 in an aortic position. When being implanted at an aortic position, the prosthesis can include a treated aortic valve (e.g., equine, porcine, bovine, human etc.). Other types of valves (e.g., other biological valves, mechanical valves or biomechanical valves) also could be used for implantation in the aortic position.

Prior to implanting the prosthesis 400, the aortic valve or at least calcified portions thereof should be removed from the aortic annulus 404. An inflow end 406 of the prosthesis 400 is annularized with respect to the annulus 404 of the aorta 408. The positioning and implantation of the prosthesis 400 can be implemented employing an implanter, such as described herein with respect to FIGS. 4-7.

For example, the patient can be placed on cardiopulmonary bypass and the cylindrical member of the implanter can be inserted through an incision in the aorta 408, such as part of an aortotomy procedure (e.g., a transverse aortotomy). The cylindrical member can then be inserted through the incision to position the distal end of the cylindrical member at a desired position relative to the annulus 404, such as shown in FIG. 6, which positioning can be guided by bulbous portions protruding from the cylindrical member. Once at the desired position, the valve can be discharged from the implanter, such that an inflow set of fingers 410 returns toward their original shape to penetrate into the annulus 404 tissue. After additional length of the prosthesis is discharged, an outflow set of fingers 412 are also released to return toward their original shape to penetrate into the annulus 404 tissue.

In the implanted position, an outflow portion 414 of the prosthesis 400 thus extends axially into the aorta 408, with the respective sets of fingers 412 and 410 cooperating to inhibit axial as well as rotational movement of the prosthesis relative to the aortic annulus 404. Additionally, lobes (or extensions) 416 extending from the outflow commissures of the valve can be attached to the sidewall of the aorta 408, such as by sutures 418. By attaching the lobes 416 to the aortic wall, improved valve competence and coaptation can be achieved, and prolapse can be mitigated.

FIG. 10 illustrates an example of a heart valve prosthesis 500 implanted in a heart 502 in a pulmonic position, such as to replace a defective or damaged pulmonic valve. In the pulmonic position, the prosthesis can include a treated pulmonic valve (e.g., equine, porcine, bovine, human, etc.). Other types of valves (e.g., other biological valves, mechanical valves or biomechanical valves) also could be used for implantation in the pulmonic position.

Prior to implanting the prosthesis 500, the pulmonic valve or at least calcified portions thereof should be removed from the pulmonic annulus 504. An inflow end 506 of the prosthesis 500 is annularized with respect to the annulus 504 of the pulmonary artery 508. The positioning and implantation of the prosthesis 500 can be implemented employing an implanter, such as described herein with respect to FIGS. 5-7.

As described above with respect to FIG. 9, the patient can be placed on cardio-pulmonary bypass and the cylindrical member of the implanter can be inserted through an incision in the pulmonary artery 508. The cylindrical member can then be inserted through the incision to position the distal end of the cylindrical member at a desired position relative to the annulus 504, such as shown in FIG. 6. Once at the desired position, the prosthesis 500 can be discharged from the implanter, such that an inflow set of fingers 510 returns toward their original shape to penetrate into the annulus 504 tissue. After additional length of the prosthesis is discharged, an outflow set of fingers 512 are also released to return toward their original shape to penetrate into the annulus 504 tissue. The respective sets of fingers thus cooperate to anchor the prosthesis relative to the annulus 504 (e.g., clamping onto the tissue at the annulus).

In the implanted position, an outflow portion 514 of the prosthesis 500 thus extends axially into the pulmonary artery 508, with the respective sets of fingers 512 and 510 cooperating to inhibit axial as well as rotational movement of the prosthesis relative to the pulmonic annulus 504. Additionally, lobes (or extensions) 516 extending from the outflow commissures of the valve can be attached to the sidewall of the pulmonary artery 508, such as by sutures 518. By attaching the lobes 516 to the pulmonary artery 508, improved valve competence and coaptation can be achieved, and prolapse can be mitigated.

Those skilled in the art will understand and appreciate that the approach described above with respect to FIGS. 9 and 10 can significantly reduce the time required for placing patients on cardio pulmonary bypass. Additionally, no sutures are required (although sutures can optionally be used) to secure the prosthesis at the annulus 404, 504 of the implantation site. Thus, the implantation can be considered "sutureless."

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A combination comprising:
   a heart valve prosthesis comprising:
      a valve member that permits substantially unidirectional flow of fluid through the valve member;
      an annular support element, having a fixed annular length, positioned generally around at least a substantial part of a sidewall portion of the valve member, the support element having axially spaced apart first and second ends;
      a first set of substantially resilient fingers extending axially and radially outwardly from the first end of the support element and curving toward the second end of the support element; and
      a second set of substantially resilient fingers extending axially and radially outwardly from the second end of the support element in a generally opposing relationship relative to the first set of fingers curving toward the first end of the support element such that distal ends of the respective fingers cross through a plane that extends through the annular support element, the first and second sets of fingers are monolithically formed with the support element, wherein the first and second sets of fingers comprise a resilient material moveable from a first condition, in which the distal ends of the first and second sets of fingers extend axially and radially to provide a generally clamp-like structure, to a second condition, in which the distal ends of the first and second sets of fingers extend generally parallel relative to the support element, the fingers being capable of returning from the second to the first condition;
      a covering of a biocompatible flexible material that extends from the support element to cover a substantial part of an axially exposed surface of at least one of the first and second sets of the fingers, the covering having first and second end portions spaced apart from each other by a generally tubular body portion that is located within the support element, the first and second end portions of the covering extending radially outwardly from the tubular body portion and connected to a respective one of the first and second sets of fingers, such that the first and second end portions are moveable with movement of the first and second sets of the fingers for covering at least part of an axially exposed surface of the first and second sets of the fingers, the first and second end portions terminating in a peripheral edge that is spaced apart from the distal ends of the respective fingers so as to cover part of the respective first and second sets of fingers; and
   an implanter that includes a cylindrical member having an interior dimension substantially commensurate with an outer diameter of the support element and operative to hold the first and second sets of fingers in the second condition while located within the cylindrical member, the first and second sets of fingers moving from the second condition to the first condition after being discharged from the cylindrical member.

2. The combination of claim 1, further comprising a bulbous portion on the outside of the cylindrical member that spans at least a part of a circumference of the cylindrical member.

3. A heart valve prosthesis comprising:
- a base portion curved about an axis and having axially spaced apart first and second ends;
- a first set of substantially resilient fingers extending axially and radially outwardly from the first end of the base portion;
- a second set of substantially resilient fingers extending axially and radially outwardly from the second end of the base portion in a generally opposing relationship relative to the first set of fingers;
- a covering formed of two annular sheets of substantially biocompatible material attached together at radially inner peripheries thereof to provide a generally tubular body portion that is located within and extends through an interior of the base portion, radially outer portions of each of the two annular sheets extending radially outwardly from respective first and second ends of the base portion so as to cover at least part of an axially exposed surface of a respective one of the first and second sets of fingers; and
- a valve located within the base portion and the tubular body portion of the covering to provide for substantially unidirectional flow of fluid through the prosthesis.

4. The prosthesis of claim 3, wherein the biocompatible material is a biological material.

5. The prosthesis of claim 3, further comprising sutures that attach the radially inner peripheries of the two annular sheets.

6. A heart valve prosthesis comprising:
- an annular support element having a fixed annular length and axially opposed first and second ends;
- a valve member positioned within the annular support element to provide for substantially unidirectional flow of fluid through the valve member;
- a first set of substantially resilient fingers extending axially and radially outwardly from the first end of the support element and curving toward the second end of the support element; and
- a second set of substantially resilient fingers extending axially and radially outwardly from the second end of the support element curving toward the first end of the support element in a generally opposing relationship relative to the first set of fingers; and
- a flexible covering having first and second end portions spaced apart from each other by a central tubular body portion that is located within the annular support element, the first and second end portions extending radially outwardly from the tubular body portion along corresponding surfaces of the respective first and second sets of fingers and terminating in a peripheral edge that is spaced apart from the distal end of the respective fingers to cover axially exposed portions of the respective first and second sets of fingers without the first and second sets of fingers penetrating through the covering.

7. The prosthesis of claim 6, wherein the resilient material comprises a shape memory alloy.

8. The prosthesis of claim 6, wherein each of the first and second end portions of the covering is connected to a respective one of the first and second sets of fingers, such that the first and second end portions of the covering are moveable as a function of movement of the first and second sets of the fingers for covering the axially exposed portions of the respective first and second sets of fingers.

9. The prosthesis of claim 6, wherein the first and second sets of fingers are monolithically formed with the support element.

10. The prosthesis of claim 9, wherein each finger of the first set of fingers comprises an elongate body having a first portion that extends from the first end of the support element axially away from the second end of the support element and a second portion that extends arcuately radially outwardly and axially from the first portion toward the second end to terminate in the distal end thereof, and wherein each finger of the second set of fingers comprises an elongate body having a first portion that extends from the second end of the support element axially away from the first end of the support element arid a second portion that extends arcuately radially outwardly and axially from the first portion toward the first end to terminate in the distal end thereof.

11. The prosthesis of claim 6, wherein the covering comprises a biological material.

12. The prosthesis of claim 6, further comprising outflow extensions at an outflow end of the valve member generally aligned with commissures of adjacent leaflets of the valve.

13. The prosthesis of claim 6, the valve member further comprising one of a biological tissue valve, a mechanical valve, and a bio-mechanical valve.

* * * * *